US010758630B2

(12) United States Patent
Sample et al.

(10) Patent No.: US 10,758,630 B2
(45) Date of Patent: Sep. 1, 2020

(54) TOPICAL COMPOSITIONS AND METHODS OF DETECTION AND TREATMENT

(71) Applicant: THE JOHNS HOPKINS UNIVERSITY, Baltimore, MD (US)

(72) Inventors: Jennifer L. Sample, Bethesda, MD (US); Julia B. Patrone, Ellicott City, MD (US); Jason J. Benkoski, Ellicott City, MD (US); Jennifer L. Breidenich, Atlanta, GA (US); Lisa A. Kelly, Ellicott City, MD (US); Huong Le, Olney, MD (US); James C. Crookston, Falls Church, VA (US); Marcia W. Patchan, Columbia, MD (US); Luis Garza, Baltimore, MD (US); Xiomara Calderon-Colon, Laurel, MD (US); Joshua T. Wolfe, Bethesda, MD (US); Mellisa L. Theodore, Nottingham, MD (US); Amanda Nelson, Hummelstown, PA (US); Sewon Kang, Phoenix, MD (US)

(73) Assignee: The Johns Hopkins University, Baltimore, MD (US)

( * ) Notice: Subject to any disclaimer, the term of this patent is extended or adjusted under 35 U.S.C. 154(b) by 401 days.

(21) Appl. No.: 13/622,666

(22) Filed: Sep. 19, 2012

(65) Prior Publication Data

US 2013/0022685 A1      Jan. 24, 2013

Related U.S. Application Data

(63) which is a continuation-in-part of application No. 13/208,874, filed on Aug. 12, 2011.

(60) Provisional application No. 61/537,225, filed on Sep. 21, 2011, provisional application No. 61/373,327, filed on Aug. 13, 2010.

(51) Int. Cl.

| A61K 49/00 | (2006.01) |
|---|---|
| A61K 9/107 | (2006.01) |
| A61K 9/00 | (2006.01) |
| A61K 47/44 | (2017.01) |

(52) U.S. Cl.
CPC ........ *A61K 49/0021* (2013.01); *A61K 9/0014* (2013.01); *A61K 9/1075* (2013.01); *A61K 47/44* (2013.01); *A61K 49/0078* (2013.01)

(58) Field of Classification Search
CPC .. A61K 49/0078; A61K 9/0014; A61K 47/44; A61K 49/0021; A61K 9/1075
See application file for complete search history.

(56) References Cited

U.S. PATENT DOCUMENTS

| 5,576,016 | A | 11/1996 | Amselem et al. |
| 5,904,932 | A | 5/1999 | De Vringer |
| 6,551,619 | B1 | 4/2003 | Penkler et al. |
| 7,507,419 | B2 | 3/2009 | Coleman, III |
| 7,544,374 | B2 | 6/2009 | Margalit et al. |
| 7,666,451 | B2 | 2/2010 | Mazzio et al. |
| 2005/0170004 | A1* | 8/2005 | Rosenberger et al. ........ 424/490 |
| 2009/0238878 | A1* | 9/2009 | Singh ....................... A61K 9/10 424/489 |
| 2010/0034873 | A1 | 2/2010 | Delprete |
| 2010/0055138 | A1 | 3/2010 | Margulies et al. |
| 2010/0062071 | A1* | 3/2010 | Loxley .................... A61K 9/10 424/489 |
| 2010/0075914 | A1 | 3/2010 | Flack et al. |
| 2011/0052704 | A1* | 3/2011 | Nazzal et al. ................ 424/489 |
| 2011/0212157 | A1* | 9/2011 | Edelson ............... A61K 9/1075 424/443 |
| 2012/0231069 | A1* | 9/2012 | Nowotnik ........ A61K 47/48107 424/450 |
| 2013/0045238 | A1* | 2/2013 | Chow et al. .................. 424/400 |

FOREIGN PATENT DOCUMENTS

| EP | 1532974 | 5/2005 |
| WO | 2005087270 | 9/2005 |
| WO | 2009106343 | 9/2009 |
| WO | 2010043346 | 4/2010 |
| WO | 2010151918 | 5/2010 |

OTHER PUBLICATIONS

Silva et al., Pharmazie 64: 177-182 (2009).*
Soheila et al., Iran. J. Chem. Chem. Eng. vol. 29, No. 4, 181-187 (2010).*
Schmidt et al. Nature, vol. 393, May 1998.*
Lee et al., Int'l J. Nanomedicine 2008:3 (4) 471-476.*

* cited by examiner

*Primary Examiner* — Robert S Cabral
(74) *Attorney, Agent, or Firm* — Noah J. Hayward

(57) ABSTRACT

A topical composition includes a nanoemulsion of a plurality of hydrophobic particles having a hydrophilic coating therein. The hydrophobic particles are derived from the same or different hydrophobic material and each hydrophobic particle has a melting point below the melting point of the respective hydrophobic material. The hydrophobic particles comprise a mean particle size of less than about 10 nm, and the nanoemulsion further includes one or more pharmaceutically active agents.

19 Claims, 3 Drawing Sheets

TOPICAL COMPOSITIONS AND METHODS OF DETECTION AND TREATMENT

CROSS-REFERENCE TO RELATED APPLICATIONS

This application claims priority to and the benefit of U.S. provisional application Ser. No. 61/537,225, filed Sep. 21, 2011, and is a continuation-in-part of co-pending U.S. patent application Ser. No. 13/208,874, filed Aug. 12, 2011, which claims priority to and the benefit of U.S. provisional application Ser. No. 61/373,327, filed Aug. 13, 2010, the contents of which are hereby incorporated by reference herein in their entireties.

GOVERNMENT INTEREST

Certain research which gave rise to the present invention was supported by the United States Air Force Contract Number 08-G-4030. Consequently, the government may retain certain rights in the invention.

BACKGROUND

Embodiments of the present invention generally relate to topical compositions and methods of detection and/or treatment.

Nanotechnology is becoming increasingly more important in the pharmaceutical, chemical and engineering fields. This is primarily due to the fact that particles made at the nanoscale have much different physical, chemical, and biological properties than larger particles. For example, in the pharmaceutical field, nanoparticles have been used to more efficiently deliver drugs, genes, diagnostics, and vaccines. Due to their small size, nanoparticles can aid in the direct entry of entrapped molecules into, for example, cells.

SUMMARY

In accordance with one or more embodiments of the present invention, there is provided a topical composition comprising a nanoemulsion of a plurality of hydrophobic particles having a hydrophilic coating therein, wherein the hydrophobic particles are derived from the same or different hydrophobic material and each hydrophobic particle has a melting point less than the melting point of the respective hydrophobic material, wherein the hydrophobic particles comprise a mean particle size of less than about 20 nm with a polydispersity of less than about 10%, and wherein the nanoemulsion further comprises at least one pharmaceutically active agent.

In accordance with another embodiment of the present invention, there is provided a topical composition comprising a nanoemulsion of a plurality of hydrophobic particles having a hydrophilic coating therein, wherein the hydrophobic particles are derived from the same or different hydrophobic material and each hydrophobic particle has a melting point less than the melting point of the respective hydrophobic material, wherein the hydrophobic particles comprise a mean particle size of less than about 10 nm, and wherein the nanoemulsion further comprises at least one pharmaceutically active agent relating to hirsutism or alopecia.

The accompanying drawings, which are incorporated in and constitute a part of this specification, illustrates one or more embodiments of the invention and, together with the description, serves to explain the principles of the invention.

BRIEF DESCRIPTION OF THE DRAWINGS

Figure 1:
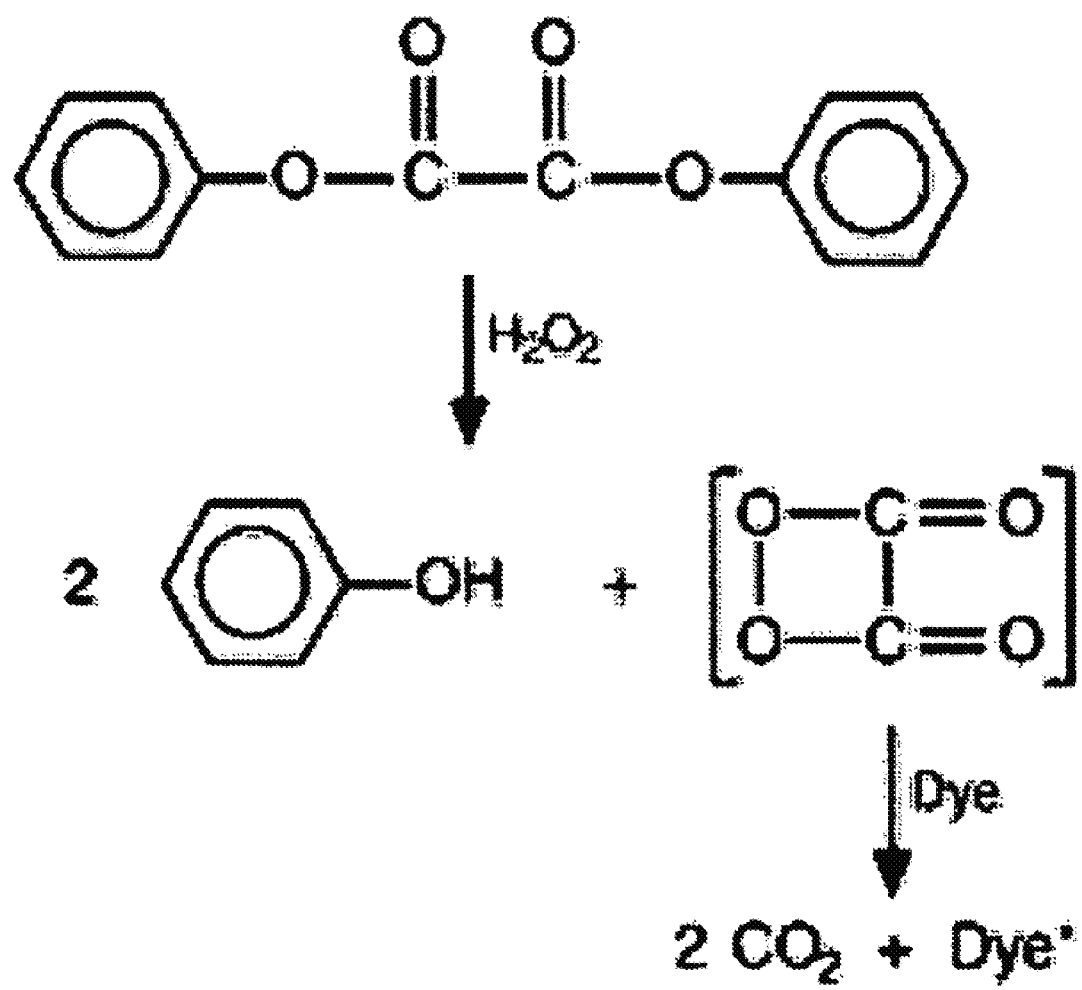
Figure 2:
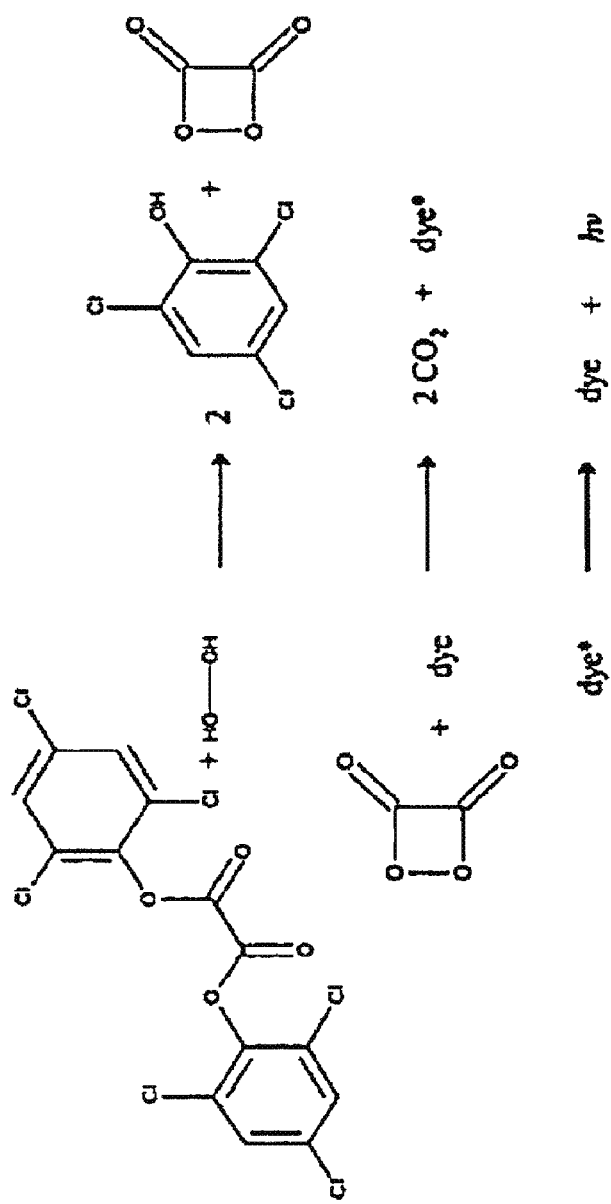

Having thus described one or more embodiments of the invention in general terms, reference will now be made to the accompanying drawings, which are not necessarily drawn to scale, and wherein:

FIGS. 1 and 2 show a chemical reaction that produces chemiluminescence; and

Figure 3:
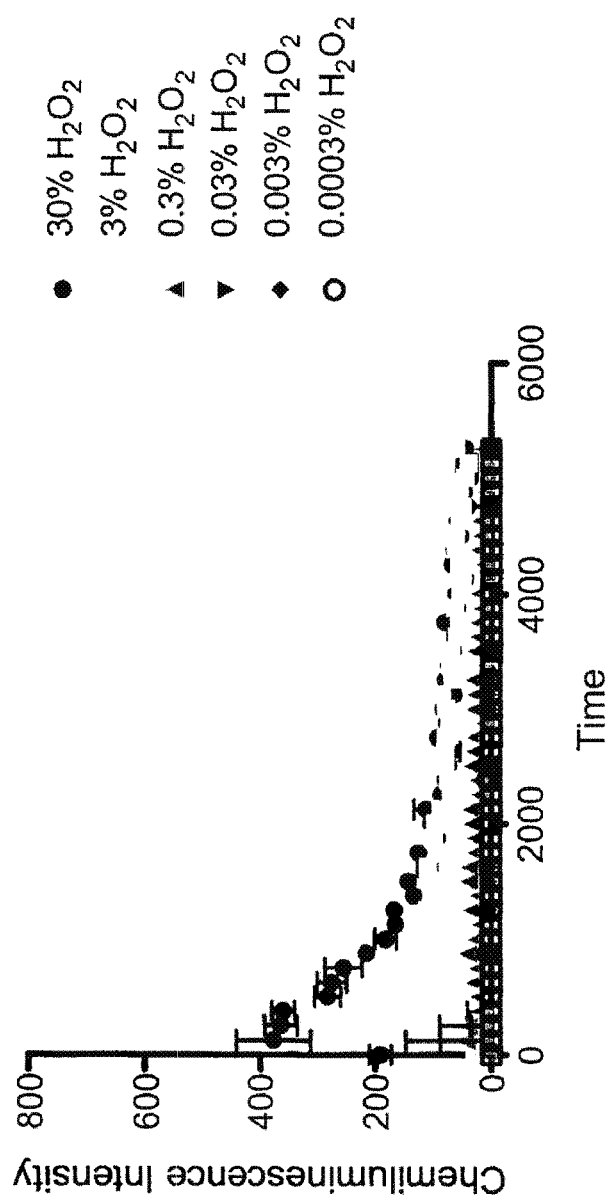

FIG. 3 is a graph showing the chemiluminescence intensity versus time for a nanoemulsion of one embodiment of the present invention.

Repeat use of reference characters in the present specification and drawings is intended to represent the same or analogous features or elements.

DETAILED DESCRIPTION

Example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements.

The term "treat" or "treating" or "treatment" of a state, disorder or condition as used herein means: (1) preventing or delaying the appearance of clinical symptoms of a state, disorder or condition developing in a host that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms i.e., prevented from happening, or stopped, e.g., terminated, such that the host no longer suffers from the state, disorder or condition, or at least the symptoms that characterize the state, disorder or condition. As such, treatment includes both curing and managing a disease condition.

The term "therapeutically effective amount" as used herein means the amount of a compound that, when administered to a subject for treating a state, disorder, condition or causing an action is sufficient to effect such treatment or action. The "therapeutically effective amount" will vary depending on the compound, the disease and its severity and the age, weight, physical condition and responsiveness of the mammal to be treated.

The term "delivering" as used herein means providing a therapeutically effective amount of one or more pharmaceutically active agents to a particular location within a host means causing a therapeutically effective blood concentration of the one or more pharmaceutically active agents at the particular location. This can be accomplished, e.g., by topical, local or by systemic administration of the one or more pharmaceutically active agents to the host.

The term "subject" or "patient" or "host" as used herein refers to mammalian animals, preferably human.

The term "topically" as used herein refers to application of the compositions according to one or more embodiments of the present invention to the surface or subsurface of the skin and mucosal cells and tissues (e.g., alveolar, buccal, lingual, masticatory, or nasal mucosa, and other tissues and cells which line hollow organs or body cavities).

Embodiments of the present invention are directed to a topical composition comprising a nanoemulsion of a plurality of hydrophobic particles having a hydrophilic coating therein, wherein the hydrophobic particles are derived from the same or different hydrophobic material and each hydrophobic particle has a melting point below the melting point of the respective hydrophobic material, and further wherein the nanoemulsion further includes one or more pharmaceutically active agents.

Hydrophobic Particles

Suitable hydrophobic materials for use in forming the hydrophobic particles include any hydrophobic material having a melting point of no more than about 85° C. In some embodiments, suitable hydrophobic material includes those having a melting point of from about 25° C. to about 37° C. In other embodiments, suitable hydrophobic material includes those having a melting point of less than about 30° C. Representative examples of such hydrophobic material include, but are not limited to, waxes and butters, oily substances with melting points above or near room temperature, including Avocado Butter, Almond Butter, Beeswax, White, Candellila Wax, Coffee Butter, Cocoa Butter, Mango Butter, Mowrah Butter, Palm Kernel Flakes, and Pistachio Butter. Waxes for use in one or more embodiments of the present invention include, but are not limited to, paraffin wax, beeswax white, candellila wax, and the like and mixtures thereof. In one embodiment, the butter comprises vegetable butters. Vegetable butters may be created by blending plant extracts with fatty fractions of the same or different plant. One such example is aloe butter, which comprises aloe extract and cocoa butter. Vegetable butters may also be obtained by blending the fatty fractions of a vegetable oil. Fatty fractions may be combined with other fatty fractions from the same or different plant source. An example of fatty fraction that may be utilized in one or more embodiments of the present invention is an unsaponifiable fraction containing paraffin, tocopherols and sterols. The percentage of the unsaponifiable fraction of a vegetable oil is usually very low and thus, unsaponifiable fractions are sometimes blended with refined vegetable oils that have undergone hydrogenation. Vegetable butters generally have a high content of symmetrical triglyceride comprising saturated and monounsaturated fatty acids, in particular stearic acid and oleic acid.

Useful butters include, but are not limited to, *mangifera indica* (mango) seed butter, aloe butter, *olea europa* (olive) butter, *coffea arabica* (coffee) bean butter, *macadamia* nut butter, *persea Gratissima* (avocado) butter, *theobroma cacao* (cocoa) seed butter, hemp seed butter, *shorea stenoptera* (illipe) seed butter, *garcinia indica* (kokum) seed butter, pistachio nut butter, *butyrospermum parkii* (shea butter), *prunus amygdalus* dulcis (sweet almond) butter, grape seed butter, *bassia latifolia* (mowrah) butter, *prunus armeniaca* (apricot) butter, *shorea robusta* (sal) butter, *glycine soja* (soy) butter, *triticum vulgare* (wheat germ) butter, palm kernel flakes and the like and mixtures thereof.

The hydrophobic particles derived from the same or different foregoing hydrophobic material include a melting point below the melting point of the respective hydrophobic material. As discussed below, the process for preparing the nanoemulsion involves adding the hydrophobic material (also referred to as the bulk hydrophobic material) together with one or more hydrophilic coating materials and one or more pharmaceutically active agents. As one skilled in the art will readily appreciate, the bulk hydrophobic material possesses a specific melting point. However, the process may be carried out such that the resulting hydrophobic particles will have a melting point below the melting point of the respective hydrophobic material. In some embodiments, the resulting hydrophobic particles may have a melting point of less than about 81° C. In additional embodiments, suitable hydrophobic material includes those having a melting point of from about 21° C. to about 33° C.

In an embodiment, the hydrophobic particles of the resulting nanoemulsions include a mean particle size of less than about 20 nm with a polydispersity of less than about 10%. In additional embodiments of the present invention, the hydrophobic particles of the resulting nanoemulsions include a mean particle size of less than about 10 nm with a polydispersity of less than about 10%. In further embodiments of the present invention, the hydrophobic particles of the resulting namoemulsions include a mean particle size of less than about 10 nm with a polydispersity of less than about 5%, 3%, 2% or 1%. The inventors of the present invention have discovered that with the methods and materials of the one or more embodiments of the present invention, the hydrophobic particles may be tailored with respect to size and polydispersity to adapt to the nanoemulsions' intended use.

In general, the amount of hydrophobic material used to form the hydrophobic particles can range from about 1% to about 10% (wt./wt.). In some embodiments, the amount of hydrophobic material used to form the hydrophobic particles ranges from about 2.5 to about 5% (wt./wt.).

Hydrophilic Coating

The hydrophilic coating may be derived from any amphiphilic material known in the art that is a pharmaceutically acceptable surfactant. Suitable amphiphilic materials include, but are not limited to, anionic, cationic, non-ionic and amphoteric surfactantsm as well as others. The term "surfactant" refers to any molecule having both a polar head group, which energetically prefers solvation by water, and a hydrophobic tail, which is not well solvated by water. For example, a "cationic surfactant" refers to a surfactant with a cationic head group, while an "anionic surfactant" refers to a surfactant with an anionic head group.

Suitable anionic surfactants that may be utilized as the hydrophilic coating include, but are not limited to, any anionic surfactant known in the art. Useful anionic surfactants include, but are not limited to, sulfates, sulfonates, phosphates, carboxylates and the like. Representative examples of anionic surfactants include alkyl or alkenyl ether sulfates, alkyl- or alkenylsulfates, sulfonate fluorosurfactants, alkylbenzenesulfonates, olefinsulfonates, alkanesulfonates, carboxylate fluorosurfactants, saturated or unsaturated fatty acid salts (soaps), alkyl or alkenyl ether carboxylates, a-sulfofatty acids, N-acylaminoacid surfactants, alkyl aryl ether phosphates, alkyl ether phosphates, phosphate mono- or diester surfactants, and sulfosuccinate ester surfactants. Examples of counter ions for the anionic residual groups in the above-described surfactants include alkali metal ions such as sodium ion and potassium ion; alkaline earth metal ions such as calcium ion and magnesium ion; ammonium ion; and alkanolamines having 1 to 3 alkanol groups each having 2 or 3 carbon atoms (for example, monoethanolamine, diethanolamine, triethanolamine, triisopropanolamine, and the like). Specific examples of such anionic surfactants may include, dioctyl sodium sulfosuccinate; perfluorooctanesulfonate (PFOS), perfluorobutanesulfonate, sodium stearate, sodium lauroyl sarcosinate, perfluorononanoate, and perfluorooctanoate (PFOA or PFO).

Suitable cationic surfactants include any cationic surfactant known in the art. Useful cationic surfactants include, but are not limited to, pH-dependent primary, secondary or tertiary amines (primary amines become positively charged at pH<10, secondary amines become charged at pH<4) and quaternary ammonium salts represented by the following formula:

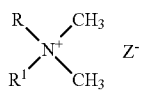

wherein Z⁻ is an anion, and R and R1 are the same or different and is hydrogen, a substituted or unsubstituted alkyl group, a substituted or unsubstituted fluoroalkyl group, a substituted or unsubstituted cycloalkyl group, a substituted or unsubstituted aryl group, a substituted or unsubstituted heteroaryl group, a substituted or unsubstituted arylalkyl group, a substituted or unsubstituted heteroarylalkyl group, or —(CH2)$_n$—R', wherein R' represents independently for each occurrence a substituted or unsubstituted cycloalkyl group, a substituted or unsubstituted aryl group, or a substituted or unsubstituted heteroaryl group and n represents independently for each occurrence an integer in the range 1 to 10 inclusive, with a proviso that at the same time, both R groups are not hydrogen atoms or benzyl groups or are not lower alkyl groups having 1 to 3 carbon atoms. In one embodiment, one of R and $R^1$ may be an alkyl group, including a linear alkyl group having 12 to 24 carbon atoms, and the other one may be a lower alkyl group having 1 to 3 carbon atoms, including a methyl group. Examples of the anion Z⁻ include halide ions such as chloride ion and bromide ion; and organic anions such as ethyl sulfate ion and methyl carbonate ion.

Representative examples of cationic surfactants include, but are not limited to, cetyl trimethylammonium chloride, cetyl trimethylammonium bromide, stearyl trimethylammonium chloride, arachyl trimethylammonium chloride, behenyl trimethylamionium chloride, cetylpyridinium chloride, polyethoxylated tallow amine, benzalkonium chloride, benzothonium chloride, 5-Bromo-5-nitro-1,3-dioxane; dimethyldioctadecylammonium chloride, dioctadecyldimethylammonium bromide, octenidine dihydrochloride and the like.

Suitable non-ionic surfactants include any non-ionic surfactant known in the art. Useful non-ionic surfactants include, but are not limited to, fatty alcohols (e.g., cetyl alcohol, stearyl alcohol, cetostearyl alohol (consisting predominantly of cetyl and stearyl alcohols), and oleyl alcohol), polyoxyalkylene alkyl ethers (e.g. BRIJ 97® and CETOMACROGOL 1000®), polyoxyalkylene alkenyl ethers, polyoxyethylene glycol octylphenol ethers (e.g., Triton X-100), polyethylene glycol alkyl ethers (e.g., octaethylene glycol monododecyl ether, and pentaethylene glycol monododecyl ether), polyglyceryl fatty acid esters, higher fatty acid mono- or diethanolamides, polyoxyethylene hydrogenated castor oil, polyoxyethylene sorbitan fatty acid esters (e.g. TWEEN 20®), polyoxyethylene fatty acid esters (e.g. MYRJ 52®), sorbitan esters (e.g. SPAN 80®), sucrose esters (e.g. WASAG ESTER 7®), alkyl-saccharide-based surfactants, alkylamine oxides, and alkylamidoamine oxides.

Suitable amphoteric surfactants include any amphoteric surfactant known in the art. Useful amphoteric surfactants include, but are not limited to, imidazoline-based amphoteric surfactants, carbobetaine-based amphoteric surfactants, amidobetaine-based amphoteric surfactants, sulfobetaine-based amphoteric surfactants, hydroxysulfobetaine-based amphoteric surfactants, and amidosulfobetaine-based amphoteric surfactants. Representative examples of amphoteric surfactants include (3-[(3-Cholamidopropyl)dimethylammonio]-1-propanesulfonate) and cocamidopropyl hydroxysultaine.

In general, the amount of hydrophilic material used to form the hydrophilic coating may vary, e.g., an amount ranging from about 1% to about 10% by weight. In one embodiment, the amount of hydrophilic material used to form the hydrophilic coating ranges from about 2.5% to about 5% by weight.

Pharmaceutically Active Agents (Drugs)

The nanoemulsion may include one or more pharmaceutically active agents incorporated therein. In the event that the drugs are hydrophobic, then the hydrophobic drugs may be incorporated into the hydrophobic particle during the production process. If the drugs are hydrophilic, then the hydrophilic drugs may be attached to the hydrophilic coating. Suitable drugs for incorporating into the nanomulsion include, but are not limited to, those that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotionsickness agents; anfiinflammatory agents; antihyperkeratolytic agents; antiperspirants; antipsoriatic agents; antiseborrheic agents; hair conditioners and hair treatment agents; antiaging and antiwrinkle agents; sunblock and sunscreen agents; skin lightening agents; depigmenting agents; vitamins; corticosteroids; tanning agents; humectants; hormones; retinoids; gum disease or oral care agents; topical cardiovascular agents; corn, callus and wart removing agents; and depilating agents. Particular drugs within the therapeutic categories can be found in standard pharmacology textbooks such as Remington: The Science and Practice of Pharmacy, (20th Ed. 2000).

Examples of the above agents include, but are not limited to, abacavir, acebutolol, acetaminophen, acetaminosalol, acetazolamide, acetohydroxamic acid, acetylsalicylic acid, acitretin, aclovate, acrivastine, actiq, acyclovir, adapalene, adefovir dipivoxil, adenosine, albuterol, alfuzosin, allopurinol, alloxanthine, almotriptan, alprazolam, alprenolol, aluminum acetate, aluminum chloride, aluminum chlorohydroxide, aluminum hydroxide, amantadine, amiloride, aminacrine, aminobenzoic acid (PABA), aminocaproic acid, aminosalicylic acid, amiodarone, amitriptyline, amlodipine, amocarzine, amodiaquin, amorolfine, amoxapine, amphetamine, ampicillin, anagrelide, anastrozole, anthralin, apomorphine, aprepitant, arbutin, aripiprazole, ascorbic acid, ascorbyl palmitate, atazanavir, atenolol, atomoxetine, atropine, azathioprine, azelaic acid, azelastine, azithiromycin, bacitracin, beclomethasone dipropionate, bemegride, benazepril, bendroflumethiazide, benzocaine, benzonatate, benzophenone, benztropine, bepridil, betamethasone dipropionate, betamethasone valerate, brimonidine, brompheniramine, bupivacaine, buprenorphine, bupropion, burimamide, butenafine, butoconazole, cabergoline, caffeic acid, caffeine, calcipotriene, camphor, candesartan cilexetil, capsaicin, carbamazepine, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clomiphene, clonidine, clopidogrel, clotrimazole, clozapine, cocaine, codeine, cromolyn, crotamiton, cyclizine, cyclobenzaprine, cycloserine, cyclosporine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamide, dopamine, dorzolamide, doxepin, doxorubicin, doxycycline, doxylamine, doxypin, duloxetine, dyclonine, econazole, eflornithine, eletriptan, emtricitabine, enalapril, ephedrine, epinephrine, epinine, epirubicin, eptifibatide, ergotarnine, erythromycin, escitalopram, esmolol, esomeprazole, estazolam, estradiol, ethacrynic acid, ethinyl estradiol, etidocaine, etomidate, famciclovir, famotidine, felodipine, fentanyl, ferulic acid, fexofenadine, FK506, flecamide, fluconazole, flucytosiine, fluocinolone acetonide, fluocinonide, 5-fluorouracil, fluoxetine, fluphenazine, flurazepam, fluvoxamine, formoterol, furosemide, galactarolactone, galactonic acid, galactonolactone, galantamine, gatifloxacin, gefitinib, gemcitabine, gemifloxacin, glycolic acid, griseofulvin, guaifenesin, guanethidine, N-guanylhistamine, haloperidol, haloprogin, hexylresorcinol, homatropine, homosalate, hydralazine, hydrochlorothiazide, hydrocortisone, hydrocortisone 21-acetate, hydrocortisone 17-butyrate, hydrocortisone 17-valerate, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loperamide, losartan, loxapine, lysergic diethylamide, mafenide, malic acid, maltobionic acid, mandelic acid, maprotiline, mebendazole, mecamylamine, meclizine, meclocycline, memantine, menthol, meperidine, mepivacaine, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, nicardipine, nicotine, nifedipine, nimodipine, nisoldipine, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate O, palonosetron, pantothenic acid, pantoyl lactone, paroxetine, pemoline, penciclovir, penicillamine, penicillins, pentazocine, pentobarbital, pentostatin, pentoxifylline, pergolide, perindopril, permethrin, phencyclidine, phenelzine, pheniramine, phenmetrazine, phenobarbital, phenol, phenoxybenzamine, phentolamine, phenylephrine, phenylpropanolarnine, phenyloin, physostigmine, pilocarpine, pimozide, pindolol, pioglitazone, pipamazine, piperonyl butoxide, pirenzepine, podofilox, podophyllin, pratipexole, pramoxine, prazosin, prednisone, prenalterol, prilocalne, procainamide, procaine, procarbazine, promazine, promethazine, promethazine propionate, propafenone, propoxyphene, propranolol, propylthiouracil, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivastigmine, rizatriptan, ropinirole, ropivacaine, salicylamide, salicylic acid, salmeterol, scopolamine, selegiline, selenium sulfide, serotonin, sertindole, sertraline, sibutramine, sildenafil, sotalol, streptomycin, strychnine, sulconazole, sulfabenz, sulfabenzamide, sulfabromomethazine, sulfacetamide, sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, tadalafil, tamsulosin, tartaric acid, tazarotene, tegaserol, telithromycin, telmisartan, temozolomide, tenofovir disoproxil, terazosin, terbinafine, terbutaline, terconazole, terfenadine, tetracaine, tetracycline, tetrahydrozoline, theobromine, theophylline, thiabendazole, thioridazine, thiothixene, thymol, tiagabine, timolol, tinidazole, tioconazole, tirofiban, tizanidine, tobramycin, tocamide, tolazoline, tolbutamide, tolnaftate, tolterodine, tramadol, tranylcypromine, trazodone, triarncinolone acetonide, triamcinolone diacetate, triamcinolone hexacetonide, triamterene, triazolam, triclosan, triflupromazine, trimethoprim, trimipramine, tripelennamine, triprolidine, tromethamine, tropic acid, tyramine, undecylenic acid, urea, urocanic acid, ursodiol, vardenafil, venlafaxine, verapamil, vitamin E acetate, voriconazole, warfarin, xanthine, zafirlukast, zaleplon, zinc pyrithione, ziprasidone, zolmitriptan and zolpidem.

The inventors have found that the nanoemulsions and resulting topical compositions have increased activity towards hair follicles when applied as a topical composition to a host. Accordingly, in embodiments of the present invention, the one or more pharmaceutically active agents may include agents known in the art for the treatment of hirsutism (excess hair), alopecia (hair loss), or other hair-related ailments or conditions. For example, in some embodiments, the one or more pharmaceutically active agents may include cyclosporine and/or FK506 for the treatment of alopecia greata. Such topical compositions of the present invention allow for the one or more pharmaceutically active agents to penetrate the basal layer of the epidermis while avoiding the concerns relating to the agents' renal toxicity. In additional embodiments, other pharmaceutically active agents known in the art that are utilized in the treatment of alopecia, hirsutism, or other hair-related ailments or conditions may be utilized in connection with one or more embodiments of the present invention. For example, minoxidil may be utilized with the nanoemulsions and resulting topical compositions to properly penetrate the epidermis for effective pharmaceutical delivery. The user's particular use of the embodiments of present invention may dictate the particular pharmaceutically active agents utilized.

The concentration of the one or more pharmaceutically active agents in the topical composition is a concentration sufficient to provide the desired cosmetic, dermatological or disease treating effect, which may vary depending on the desired cosmetic condition, dermatological disorder or disease being treated, the size of the patient, and other factors. In general, the concentration of the one or more pharmaceutically active agent can range from about 0.01% to about 20% by weight, based on the total weight of the oil phase. In one embodiment, the concentration of the one or more pharmaceutically active agent can range from about 1 to about 10% by weight, based on the total weight of the oil phase (e.g., wax or butter).

Chemiluminescent Disease-Detecting Systems

The nanoemulsion may also include one or more chemiluminescent disease-detecting systems incorporated therein for detecting a disease or condition in a host. For example, hydrogen peroxide ($H^2O^2$) is a reactive oxygen metabolic by-product that may serve as a regulator for a number of oxidative stress related states. Hydrogen peroxide is believed to be over-produced by cells at the early stages of most diseases such as asthma, inflammatory arthritis, atherosclerosis, diabetic vasculopathy, osteoporosis, and a number of neurodegenerative diseases. In addition, overproduction of hydrogen peroxide may occur in the development of damage caused to skin by exposure to ultraviolet radiation. Thus, detecting low levels of hydrogen peroxide in the skin could serve as an early warning indicator for skin cancer. The topical composition in one or more embodiments of the present invention may therefore be used as a diagnostic tool for detecting diseases.

Accordingly, in one embodiment, the one or more chemiluminescent disease-detecting systems include a peroxide-reactive compound and a light-emitting material. By incorporating a peroxide-reactive compound and a light-emitting material into the hydrophobic particle, a three-component reaction in vivo may advantageously be achieved. When the hydrophobic particles bump into hydrogen peroxide, they will excite the light-emitting material, e.g., dye, which then emits photons that exhibits chemiluminescence in the presence of the peroxide. Thus, if a doctor would see a significant amount of chemiluminescence in the area in which the topical composition was applied, the doctor may know that the patient may be presenting early signs of a disease in that area of the body.

In one embodiment, a suitable peroxide-reactive compound is an oxalate ester. Useful oxalate esters include compounds represented by the formula:

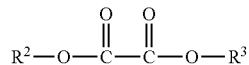

wherein $R^2$ and $R^3$ are independently a substituted or unsubstituted aryl group, or a substituted or unsubstituted heteroaryl. The aryl or heteroaryl group may be substituted with, for example, hydrogen, hydroxy, halide (e.g., chloride, bromide, fluoride, etc.), a carbonyl group, an optionally substituted amine, optionally substituted alkyl, optionally substituted alkoxy, cyano, and/or nitro group. Representative examples of heteroaryl groups for use herein include, by way of example, a substituted or unsubstituted stable 3 to about 30 membered ring radical, containing carbon atoms and from one to five heteroatoms, e.g., nitrogen, phosphorus, oxygen, sulfur and mixtures thereof. Suitable heteroaryl groups may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states.

Representative examples of oxalate esters include, but are not limited to, iptycene compounds, bis(2-carbopentyloxy-3,5,6-trichlorophenyl) oxalate, bis(2-nitrophenyl) oxalate, bis(2,4-dinitrophenyl) oxalate, bis(2,6-dichloro-4-nitrophenyl) oxalate, bis(2,4,6-trichlorophenyl) oxalate, bis(3-trifluoromethyl-4-nitrophenyl) oxalate, bis(2-methyl-4,6-dinitrophenyl) oxalate, bis(1,2-dimethyl-4,6-dinitrophenyl) oxalate, bis(2,4-dichlorophenyl) oxalate, bis(2,5-dinitrophenyl) oxalate, bis(2-formyl-4-nitrophenyl) oxalate, bis(pentachlorophenyl) oxalate, bis(pentafluorophenyl) oxalate, bis (1,2-dihydro-2-oxo-1-pyridyl) glyoxal, bis-N-phthalmidyl oxalate, bis(6-carbopentoxy-2,4,5-trichlorophenyl) oxalate (CPPO), bis(2,4,5-trichloro-6-carbobutoxyphenyl) oxalate, bis(2,4,6-trichlorophenyl) oxalate (TCPO), bis(2,4,5-trichloro-6-carbopentoxyphenyl) oxalate, bis(2,4,5-trichloro-6-carbobutoxyphenyl) oxalate, bis(2,4,6-trichlorophenyl) oxalate, 1,1-oxalyldiimidazole and phthalimido 3,6, 6-trisulfo-2-naphthyl oxalate.

Other examples of peroxide-reactive compounds include 5-amino-2,3-dihydrophthalazine-1,4-dione or 3-aminophthalhydrazide (luminol), Cyalume® (containing diphenylethandioate, a dye, and other components) 2,4,5-triphenylimidazole (lophine), 10,10'-dialkyl-9,9'-biacridinium salts (lucigenin), and 9-chlorocarbonyl-10-methylacridinium chloride (rosigenin), and the like. In one embodiments, the peroxide-reactive compound is bis(2,4,6-trichlorophenyl) oxalate, bis(2-carbopentyloxy-3,5,6-trichlorophenyl) oxalate, oxalic acid, bis[2,4,5-trichloro-6-(pentyloxycarbonyl)phenyl]ester and bis (pentafluorophenyl) oxalate. In one embodiment, bis(2,4,6-trichlorophenyl) oxalate is the peroxide-reactive compound. In another embodiment, bis(2-carbopentyloxy-3,5,6-trichlorophenyl) oxalate is the peroxide-reactive compound.

In some embodiments, the peroxide-reactive compound may incorporated into the nanoemulsion in an amount ranging from about 1% to about 20% by weight of the hydrophobic oil phase. In further embodiments, the peroxide-reactive compound is incorporated into the nanoemulsion in an amount ranging from about 10% to about 20% by weight of the oil phase.

Suitable light-emitting materials may be any luminescent material, including dyes, oligomers, polymers, and the like combinations thereof. The light-emitting material may be selected to exhibit certain properties, such as a particular emission wavelength, high quantum yield, high output light efficiency when formulated in a peroxide reactive system, and/or compatibility (e.g., solubility) with one or more components of the nanoemulsion. In one embodiment, the light-emitting material may be selected to exhibit a high quantum yield, for example, when present in a nanoemulsion having a high concentration of light-emitting material. As used herein, the "quantum yield" of a material refers to the total emission produced by the material, i.e., the number of photons emitted per absorbed photon. In some embodiments, the light emitting material may be selected to exhibit a high output light efficiency when formulated in a peroxide reactive system. As used herein, "output light efficiency" of a material in the nanoemulsion refers to the yield of output light (e.g., observable light) produced by the nanoemulsion in the presence of a peroxide, i.e., the efficiency of the interaction between the peroxide and the system in generating light.

In some cases, light-emitting materials may be any compound which has a determinable emission of light (e.g., chemiluminescence, fluorescence, phosphorescence), with an emission spectrum between, for example, about 400 to about 800 nm. In one embodiment, the light-emitting material is a fluorescent dye. In another embodiment, suitable light-emitting materials include, but are not limited to, anthracene, benzanthracene, phenanthrene, naphthacene, pentacene, diphenylanthracene, 9,10-bis(phenylethynyl)anthracene, substituted derivatives thereof, and the like. Examples of substituents include phenyl, lower alkyl, halide, cyano, alkoxy, and other substituents which do not interfere with the light-emitting reaction described herein.

In one embodiment, the light-emitting material may be a conjugated polymer, such as poly(phenylene-ethynylene), poly(phenylene-vinylene), poly(p-phenylene), polythiophene, other poly(arylene)s, substitute derivatives thereof, and the like. The light-emitting capability of such polymers are known in the art, and may be selected to suit a particular application.

In one embodiment, the light-emitting material may be covalently bound to the peroxide-reactive material. In some embodiments, the light-emitting material may be covalently bound to the hydrophobic particle.

In some embodiments, the light-emitting material is incorporated into the nanoemulsion in an amount ranging from about 0.01 to about 10 mg/ml based on the volume of the hydrophobic material. In further embodiments, the light-emitting material is incorporated into the nanoemulsion in an amount ranging from about 0.1 to about 1 mg/ml based on the volume of the hydrophobic material.

FIGS. 1 and 2 show a chemical reaction that produces chemiluminescence. In general, the mechanism is that first the phenyl oxalate ester and hydrogen peroxide ($H_2O_2$) react to form a peroxy acid ester and phenol; and then the peroxy acid ester decomposes to form more phenol and a highly energetic intermediate, presumed to be a cyclic compound containing a four-membered ring dimer of $CO_2$. As the cyclic dimer decomposes into two $CO_2$ molecules, it gives up its energy to a waiting dye molecule, which then fluoresces.

As shown in FIG. 2, the chemical reaction taking place includes a solution of a phenyl oxalate ester (commonly bis(2,4,5-trichlorophenyl-6-carbopentoxyphenyl)oxalate (CPPO), a fluorescent dye that determines the color of light, and hydrogen peroxide ($H_2O_2$). The hydrogen peroxide reacts with the phenyl oxalate ester producing carbon dioxide, a phenol and, most importantly, releasing energy. This energy is absorbed by the dye, exciting electrons in the dye's molecules to a higher energy level. Once at the higher energy level, the electrons immediately lose the energy they absorbed and fall to lower energy levels. As the electrons fall back to lower energy levels, the energy that is lost is transformed into electromagnetic radiation, some of which is visible light.

The dye must gain energy from the breakdown of the CPPO. For light to be seen in the visible spectrum, the radiation emitted must be between 400 nm and 700 nm. This range of wavelengths has a corresponding range of energy required between 170 kJ/mol and 300 kJ/mol. This energy is released from a high energy intermediate that forms during the reaction and is transferred to the dye. The intermediate that forms when the CPPO is oxidized by hydrogen peroxide is called 1,2-dioxetane-3,4-dione. This compound is a four membered ring structure. As in most four membered rings, the compound is considered high in energy because of the strain on the bonds of the molecule forcing them into the ring. Although the compounds are different, they all share the common trait of being highly conjugated systems. This conjugation allows electrons to move easily because of the small gap between the highest occupied molecular orbital (HOMO) and the lowest unoccupied molecular orbital (LUMO). The energy produced as the four-membered ring structure decomposes into two $CO_2$ molecules is enough to move the electrons across the gap.

Since the color of the light depends on the fluorescer selected, peroxyoxalate chemiluminescence may be formulated in many desired colors. For example, a blue color may be produced using 9,10 diphenylanthracene, green color can be produced using 9,10-bis(phenylethynyl)anthracene, and yellow may be produced using either of 1-chloro-9,10-bis (phenylethynyl)anthracene or Rubrene [5,6,11,12-tetraphenylnaphthacene], orange may be produced using 5,12-bis (phenylethynyl)-napthacene.

In another embodiment, the chemiluminescent disease-detecting systems may detect a number of other biomarkers when combined with an appropriate source of energy capable of converting an enzyme that catalyzes an oxidation-reduction reaction to obtain hydrogen peroxide. In an embodiment, a suitable source is an oxidase. An oxidase is any enzyme that catalyzes an oxidation-reduction reaction involving molecular oxygen ($O_2$) as the electron acceptor. In these reactions, oxygen is reduced to hydrogen peroxide ($H_2O_2$). For example, glucose oxidase (GOx) is an enzyme that catalyzes the oxidation of β-D-glucose to D-glucono-1,5-lactone with $O_2$ as the electron and proton acceptor, creating hydrogen peroxide ($H_2O_2$) as a byproduct. In such embodiment, a concentration of glucose in the presence of the GOx is established.

Suitable sources of energy for use herein include, but are not limited to, one or more of malate oxidase, hexose oxidase, glucose oxidase, glutamate oxidase, cholesterol oxidase, aryl-alcohol oxidase, L-gulonolactone oxidase, galactose oxidase, pyranose oxidase, L-sorbose oxidase, pyridoxine 4-oxidase, alcohol oxidase, catechol oxidase, (S)-2-hydroxyacid oxidase, ecdysone oxidase, choline oxidase, secondary-alcohol oxidase, 4-hydroxymandelate oxidase, long-chain-alcohol oxidase, glycerol-3-phosphate oxidase, thiamine oxidase, hydroxyphytanate oxidase, nucleoside oxidase, N-acylhexosamine oxidase, polyvinyl-alcohol oxidase, D-arabinono-1,4-lactone oxidase, vanillyl-alcohol oxidase, nucleoside oxidase, D-mannitol oxidase, xylitol oxidase, monoamine oxidase, xanthine oxidase such as hypoxanthine, L-gulonolactone oxidase, and lysyl oxidase and the like and mixtures thereof.

Process for Preparing the Nanoemulsion

The nanoemulsions formed herein are an emulsified system which undergoes a phase transition from a water-in-oil (W/O) emulsion to an oil-in-water (O/W) emulsion. At the phase inversion temperature, the interfacial tension between water and oil reaches a minimum. If the system is agitated during this minimum, the continuous oil phase breaks up into nanoscopic droplets. Thus, to obtain the nanoemulsion described herein, an oil/water/surfactant system containing the foregoing components, i.e., hydrophobic material, hydrophilic material, drug and/or chemiluminescent disease-detecting system and optional penetration enhancing compounds is heated above the phase inversion temperature, e.g., a temperature ranging from about 30° C. to about 90° C., and then stirred while it cools back to room temperature. To obtain the solid hydrophobic particles with a hydrophilic coating, the melting point of the oil phase is kept below the phase inversion temperature, e.g., a temperature ranging from about 15° C. to about 80° C. Methods for obtaining such a nanoemulsion are described, for example, in Forgiarini et al., "Studies of the relation between phase behavior and emulsification methods with nanoemulsion formation", Colloidal Polym. Sci. Vol 115, pp. 36-39 (2000); Tadros et al., "Formation and stability of nano-emulsions", Elsevier, Advances in Colloidal And Interface Science, pp. 303-318 (2004), and Forgiarini et al., "Formation of Nano-emulsions by Low-Energy Emulsification Methods at Constant Temperature", Langmuir Vol. 17, pp. 2076-2083 (2001), the contents of which are incorporated by reference herein.

Topical Compositions

The topical compositions in one or more embodiments of the present invention may further contain one or more pharmaceutically acceptable excipients or carriers. Suitable pharmaceutically acceptable excipients or carriers include thickening agents, pigments, preservatives, pH adjusting agents, hydrating agents, ultraviolet-absorbing agents, and the like.

A thickening agent may be, for example, a polymer that is water soluble or that generates a colloidal solution in water. Useful thickening agents include, but are not limited to, polymers or copolymers unsaturated carboxylic acids or unsaturated esters, polysaccharide derivatives, gums, colloidal silicates, polyethylene glycols (PEG) and their derivatives, polyvinylpyrrolidones and their derivatives, polyacrylamides and their derivatives, polyacrylonitriles, hydrophilic silica gels, or mixtures thereof. Examples of thickening agents include acrylic and/or methacrylic polymers or copolymers, vinylcarboxylic polymers, polyglyceryl acrylates or methacrylates, polyacrylamides derivatives, cellulose or starch derivatives, chitin derivatives, alginates, hyaluronic acid and its salts, chonodroitin sulphates, xanthan, gellan, Rhamsan, karaya or guar gum, carob flour, and colloidal aluminum magnesium silicates of the montmorillonite type.

In one embodiment, a thickening agent includes vinylcarboxylic polymers sold under the tradename CARBOPOL® (Goodrich), acrylic acid/ethyl acrylate copolymers, acrylic acid/stearyl methacrylate copolymers, carboxymethylcellulose, hydroxymethylcellulose, hydroxypropylcellulose, microcrystalline cellulose, hydroxypropyl guar, colloidal hectorites, bentonites, and the like.

Suitable pigments include, but are not limited to, inorganic pigments, organic pigments, or nacreous pigments. Examples of inorganic pigments include titanium dioxide, black, yellow, red or brown iron oxide, manganese violet, ultramarine violet, ultramarine blue, chromium oxide, and the like. Examples of organic pigments include D & C Red No. 3, No. 6, No. 7, No. 9, No. 13, No. 19, No. 21, No. 27, No. 30, or No. 36, or alternatively carbon black. Examples of nacreous pigments include white nacreous pigments, such as mica coated with titanium oxide or with bismuth oxychloride. Colored nacreous pigments, such as titanium mica colored with iron oxides or with chromium oxide, titanium mica colored with an organic pigment of the above-mentioned type, or alternatively, nacreous pigments based on bismuth oxychloride, also can be used.

A preservative may be used to prevent, for example, bacterial attack. Suitable preservatives include, but are not limited to, butylparaben, propylparaben, chlorocresol, sorbic acid, benzoic acid and the like and mixtures thereof.

Suitable basic pH adjusters include, but are not limited to, ammonia; mono-, di-, and tri-alkyl amines; mono-, di-, and tri-alkanolamines; alkali metal and alkaline earth metal hydroxides; and mixtures thereof. Examples of basic pH adjusters include ammonia; sodium, potassium, and lithium hydroxide; monoethanolamine; triethylamine; isopropanolamine; diethanolamine; and triethanolamine.

Suitable acidic pH adjusters include, but are not limited to, mineral acids, organic carboxylic acids and the like. Examples of mineral acids include citric acid, hydrochloric acid, nitric acid, phosphoric acid, and sulfuric acid.

In one embodiment, the topical compositions may be formulated in a semi-liquid formulation. Examples of such topical compositions include, but are not limited to, a topical solution, spray, mist, drops and the like. Accordingly, the topical compositions may be administered by way of injection by needle into a certain area of the body in the case where it is a topical solution. If the nanoemulsion encounters hydrogen peroxide, the hydrophobic particles would emit light.

In one embodiment, the topical compositions may be in a semisolid form such as, for example, gels, creams, lotions, suspensions, emulsions, ointments, foams, pastes and the like. Thus, the topical compositions can be administered by way of a transdermal patch or can be applied to directly to area of the body in need of treatment.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable-bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Creams, as also well known in the art, are viscous liquids or semi-solid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

As will be readily be understood by those skilled in the field of pharmaceutical formulation, gels are semi-solid, suspension-type systems. Gel forming agent for use herein may be any gelling agent typically used in the pharmaceutical art for topical semi solid dosage forms. Single-phase gels contain organic macromolecules distributed substantially uniformly throughout the carrier liquid, which is typically aqueous, but also can contain an alcohol and optionally an oil. In order to prepare a uniform gel, dispersing agents such as alcohol or glycerin can be added, or the gelling agent can be dispersed by tritration, mechanical mixing or stirring, or combinations thereof. The amount of gelling agents may vary and may range from about 0.1% to about 2.0% by weight, based on the total weight of the composition. The gel forming agent also works by the principle of copolymerization. Under alkaline pH, carbomer in presence of water undergoes cross linking and forms a gel like structure. The degree of polymerization is dependent upon the pH. At a threshold pH, the viscosities achieved by the polymer grade is the maximum.

Lotions, are preparations to be applied to the skin surface without friction, and are typically semi-liquid preparations in which solid particles, including the active agent, are present in a water or alcohol base. Lotions are usually suspensions of solids, and preferably, for the present purpose, comprise a liquid oily emulsion of the oil-in-water type. Lotions are formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semi-solid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

In one embodiment, the topical compositions may be used to treat a disease condition by applying a therapeutically effective amount of the topical composition to the area in need of treatment; wherein the nanoemulsion includes one or more pharmaceutically active agents. By applying the topical composition to the area of the host in need of treatment, the solid hydrophilic particles may melt and be absorbed into the skin. As indicated above, the hydrophilic particles are of an appropriate size to diffuse more deeply into the skin than larger particles. In this manner, the one or more pharmaceutically active agents may be released from the nanoemulsion and treat the disease condition.

The topical compositions in one or more embodiments of the present invention may be used to treat a wide variety of disease conditions or disorders as long as the disease or disorder is capable of being treated with a topical dermatological agent or at least suspected of being treatable with a topical dermatological agent. As noted above, in certain embodiments, a dermatological agent is not employed. The topical compositions in one or more embodiments of the present invention are suited to treat disease conditions that affect the skin and thus may be characterized as skin conditions or dermatological conditions. As used herein, the term "skin condition" and analogous terms are used broadly to refer to any condition of the skin in need of treatment, including those that do not involve inflammation of the skin, e.g., vitiligo. These skin disorders may be the result of a bacterial infection, viral infection, fungal infection, autoimmune response, allergenic response, idiopathic, and the like and may be acute or chronic lasting from a few minutes to a lifetime.

Accordingly, the topical compositions in one or more embodiments of the present invention can be used to treat any disease condition including those that originate at or are localized to the skin, as well as disease conditions that originate elsewhere in the body and/or are not localized to the skin. In other words, disease conditions that may affect the skin may originate in another organ or system of the body, but may have manifestations or symptoms that affect the skin. Disease conditions that may be treated in accordance with one or more embodiments of a method of the present invention include, but are not limited to, alopecia, hirsutism, psoriasis, eczema, vitiligo, atopic dermatitis, contact dermatitis, nummular dermatitis, generalized exfoliative dermatitis, stasis dermatitis, perioral dermatitis, morphoca, palmoplantar pustulosis, ichthyosis, keratoderma, warts, porokeratosis, Hailey-Hailey disease, pityriasis rubra pilaris, acanthosis nigricans, rosacea, lupus erythmatosus, Lichen simplex chronicus (neurodermatitis), alopecia, seborrheia, actinic keratosis, corns, pruritis, sun burn, urticaria, localized scratch dermatitis, staphylococcal disorders, ertsipelas, folliculitis, carbuncles, furuncles, erythrasma, candidiasis, dermatophyte infections, scabies, pediculosis, hypertrichosis, lichen planus, etc.

In another embodiment, the topical compositions can be used to detect a disease or a condition in need of treatment. In general, an effective amount of a topical composition is contacted with a host; wherein the topical composition comprises a nanoemulsion of a plurality of hydrophobic particles having a hydrophilic coating therein, wherein the hydrophobic particles are derived from the same or different hydrophobic material and has a melting point below the melting point of the respective hydrophobic material, and further wherein the nanoemulsion further includes one or more chemiluminescent disease-detecting systems. As discussed above, the one or more chemiluminescent disease-detecting systems can be used to detect, for example, diseases such as asthma, inflammatory arthritis, atherosclerosis, diabetic vasculopathy, osteoporosis, a number of neurodegenerative diseases, skin cancer and the like.

It is further within the scope of the invention to provide a kit containing the apparatus and/or reagents necessary to carry out the test method of detecting a disease or a condition in need of treatment in the field. A complete kit would contain all of the equipment and consumables for conducting at least one test procedure. Thus, such a kit would include at a minimum a source of a topical composition comprising a nanoemulsion of a plurality of hydrophobic particles having a hydrophilic coating therein, wherein the hydrophobic particles are derived from the same or different hydrophobic material and has a melting point below the melting point of the respective hydrophobic material, and further wherein the nanoemulsion further includes one or more chemiluminescent disease-detecting systems; and (b) a light emitting detector for detecting a disease or a condition in the host. In general, light emitting detectors include CCD cameras, photodiodes, UV-vis spectrometers, and hyperspectral cameras.

The following examples are provided to enable one skilled in the art to practice the invention and are merely illustrative of the invention. The examples should not be read as limiting the scope of the invention as defined in the claims.

Example 1

Preparation of a Nanoemulsion

Into a 4 ml vial was dissolved a fluorescent dye, 9,10-bis (phenylethynyl)-antracene (1 mg), the active chemiluminescent material, 1-1'-oxalyldiimidazole (940 mg), methyl alcohol (950 ul), and decyl alcohol (50 ul). Next, the surfactant, Brij 97 (110 mg) and the wax, eicosane (100 mg), was added to the mixture. The mixture was heated to 60° C., above the melting point of eicosane and mixed until uniform. Distilled water (1.7 g) was added to the oily mixture. The vial was heated again to 60° C. and then the mixture was stirred continuously and allowed to cool to room temperature such that a phase inversion temperature was seen by noting the transition between a cloudy suspension at high temperatures, and a transparent nanoemulsion at room temperature. The particle size of the hydrophobic particles was 8 nm as determined by dynamic light scattering.

Example 2

Toxcity Testing

The nanoemulsion of Example 1 was then tested for toxicity. Human keratinocytes (HaCaT, Cell Lines Service) were cultured in Dulbeco's modified Eagle's medium with glucose and L-glutamine, without sodium pyruvate (Mediatech), 10% fetal bovine serum, 100 U/ml penicillin, and 100 µg/ml streptomycin. Cells were maintained in a humidified atmosphere at 37° C., 5% $CO_2$ and passaged at 80% confluence. HaCaT cells (MTT assay) were plated at a density of $4 \times 10^4$ cells/well and allowed to equilibrate at 37° C. overnight. Next, 5 µl/well of the nanoemulsion of Example 1 was added to each replicate well. After 18 hours of exposure to the nanoemulsion preparation, cellular health was determined using the MTT assay, according to the manufacturer's instructions (ATCC). Briefly, MTT assay was added to the wells of the microplate and after two hours of incubation at 37° C., intracellular formazin crystals were solubilized with the manufacturer's detergent solution (ATCC). Absorbance values were obtained using the Safire2 microplate reader (Tecan US, Raleigh, N.C.) with a measurement wavelength of 570 nm and a reference wavelength of 700 nm, read from the bottom.

Example 3

Chemiluminescence from exogenously added hydrogen peroxide was measured using the Tecan Safire2 microplate reader. The nanoemulsion (100 µl) of Example 1 was pipetted into six wells of a white, flat-bottom, 96-well microtiter plate. Various amount of hydrogen peroxide ($H_2O_2$) (i.e., 0.0003, 0.003% $H_2O_2$, 0.03% $H_2O_2$, 0.3% $H_2O_2$, 3% $H_2O_2$ and 30% $H_2O_2$) was diluted in distilled water and 5 µl of the diluted solution was added to each appropriate well. Sample chemiluminescence was immediately read using the Safire2 microplate reader (Tecan US, Raleigh, N.C.) and was measured every two minutes for sixty minutes. Values for duplicate wells were averaged and the standard deviation determined. FIG. 3 shows the results of the measurements.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A topical composition comprising a nanoemulsion of a plurality of hydrophobic particles having a hydrophilic coating therein, wherein
   the hydrophobic particles are derived from the same or different bulk hydrophobic material and each hydrophobic particle has a melting point less than the melting point of the respective bulk hydrophobic material,
   the hydrophobic particles comprise a mean particle size of less than 8 nm, said hydrophilic coating consists of one or more non-ionic surfactants, and the nanoemulsion further comprises at least one pharmaceutically active agent;
   wherein the bulk hydrophobic material has a melting point of from about 21° C. to about 33° C.

2. The topical composition of claim 1, wherein the hydrophobic particles comprise a mean particle size of less than 8 nm with a polydispersity of less than about 5%.

3. The topical composition of claim 1, wherein the hydrophobic particles comprise a mean particle size of less than 8 nm with a polydispersity of less than about 3%.

4. The topical composition of claim 1, wherein the hydrophobic material is selected from the group consisting of a wax, butter and combinations thereof.

5. The topical composition of claim 1, wherein the one or more non-ionic surfactants is selected from the group consisting of a fatty alcohol, a polyoxyalkylene alkyl ether, a polyoxyalkylene alkenyl ether, a polyoxyethylene glycol octylphenol ether, a polyethylene glycol alkyl ether, a polyglyceryl fatty acid ester, a fatty acid mono- or diethanolamide, a polyoxyethylene hydrogenated castor oil, a polyoxyethylene sorbitan fatty acid ester, a polyoxyethylene fatty acid ester, a sorbitan ester, a sucrose ester, an alkylsaccharide-based surfactant, an alkylamine oxide, an alkylamidoamine oxide and mixtures thereof.

6. A topical composition comprising a nanoemulsion of a plurality of hydrophobic particles having a hydrophilic coating therein, wherein the hydrophobic particles are derived from the same or different bulk hydrophobic material and each hydrophobic particle has a melting point less than the melting point of the respective bulk hydrophobic material, said hydrophilic coating consists of one or more non-ionic surfactants; wherein the hydrophobic particles comprise a mean particle size of less than 8 nm, and wherein the nanoemulsion further comprises at least one pharmaceutically active agent relating to hirsutism or alopecia and; wherein the bulk hydrophobic material has a melting point of from about 21° C. to about 33° C.

7. The topical composition of claim 6, wherein the hydrophobic particles comprise a mean particle size of less than 8 nm with a polydispersity of less than about 10%.

8. The topical composition of claim 6, wherein the hydrophobic particles comprise a mean particle size of less than 8 nm with a polydispersity of less than about 5%.

9. The topical composition of claim 6, wherein the at least one pharmaceutically active agent relating to hirsutism or alopecia comprises cyclosporine, FK506, minoxidil, or mixtures thereof.

10. The topical composition of claim 6, wherein the hydrophobic material is selected from the group consisting of a wax, butter and combinations thereof.

11. A method for treating hirsutism or alopecia, the method comprising contacting an area of a host with a therapeutically effective amount of a topical composition comprising a nanoemulsion of a plurality of hydrophobic particles having a hydrophilic coating therein, wherein
the hydrophobic particles are derived from the same or different bulk hydrophobic material and each hydrophobic particle has a melting point less than the melting point of the respective bulk hydrophobic material,
the hydrophobic particles comprise a mean particle size of less than 8 nm,
said hydrophilic coating consists of one or more non-ionic surfactants, and
the nanoemulsion further comprises at least one pharmaceutically active agent relating to hirsutism or alopecia;
wherein the bulk hydrophobic material has a melting point of from about 21° C. to about 33° C.

12. The method of claim 11, wherein the at least one pharmaceutically active agent relating to hirsutism or alopecia comprises cyclosporine, FK506, minoxidil, or mixtures thereof.

13. The topical composition of claim 1, further comprising a chemiluminescent detecting system comprising a peroxide-reactive compound and a light-emitting material.

14. The topical composition of claim 1, further comprising a preservative.

15. The topical composition of claim 14, wherein the preservative comprises butylparaben, propylparaben, chlorocresol, sorbic acid, benzoic acid, or combinations thereof.

16. The topical composition of claim 1, wherein the topical composition is loaded onto a transdermal patch.

17. The method of claim 11, wherein the topical composition is loaded onto a transdermal patch and said step of contacting an area of a host with a therapeutically effective amount of a topical composition comprises applying the transdermal patch onto the area.

18. The topical composition of claim 6, further comprising a preservative.

19. The method of claim 11, wherein the topical composition further comprises a preservative.

* * * * *